United States Patent
Kammer et al.

(10) Patent No.: US 7,874,167 B2
(45) Date of Patent: Jan. 25, 2011

(54) METHOD AND APPARATUS FOR PRODUCING SLUSH FOR SURGICAL USE

(75) Inventors: Patrick Kammer, Greensboro, NC (US); Kevin Joseph Rackers, Summerfield, NC (US)

(73) Assignee: C Change Surgical LLC, Winston-Salem, NC (US)

( * ) Notice: Subject to any disclaimer, the term of this patent is extended or adjusted under 35 U.S.C. 154(b) by 0 days.

(21) Appl. No.: 12/477,635

(22) Filed: Jun. 3, 2009

(65) Prior Publication Data

US 2009/0301107 A1    Dec. 10, 2009

Related U.S. Application Data

(60) Provisional application No. 61/059,732, filed on Jun. 6, 2008.

(51) Int. Cl.
*F25C 1/00*    (2006.01)
(52) U.S. Cl. .............................. 62/68; 62/342; 62/457.5; 366/220; 366/209; 366/218
(58) Field of Classification Search .................. 62/342, 62/457.4, 457.5, 404–426, 457.1–457.9, 62/68; 366/235, 237, 209–222
See application file for complete search history.

(56) References Cited

U.S. PATENT DOCUMENTS

| 714,415 | A | * | 11/1902 | Trafford | 366/214 |
| 2,555,624 | A | * | 6/1951 | Anderson | 62/342 |
| 2,993,350 | A | * | 7/1961 | Smith | 62/342 |
| 3,998,070 | A | | 12/1976 | Mueller | |
| 4,393,659 | A | | 7/1983 | Keyes et al. | |
| 4,526,012 | A | | 7/1985 | Chigira | |
| 4,580,405 | A | * | 4/1986 | Cretzmeyer, III | 62/63 |

(Continued)

FOREIGN PATENT DOCUMENTS

JP    06-12353 A    5/1994

(Continued)

OTHER PUBLICATIONS

International Search Report and Written Opinion From Corresponding PCT Application No. PCT/US2009/0462902, Jan. 20, 2010, (14 pgs).

(Continued)

*Primary Examiner*—William E Tapolcai
(74) *Attorney, Agent, or Firm*—The Eclipse Group LLP; Kevin E. Flynn

(57) ABSTRACT

Methods and apparatus for producing saline slush for surgical applications. Producing surgical saline slush in a slush bottle that is a rigid or semi-rigid, high integrity, sturdy container that resists punctures and leaks to better maintain a sterile barrier and does not rely on having an external object placed in the fluid to mix the slush. Slush is agitated by rotating the slush bottle within a slush bottle carriage around an axis of rotation. Agitation of the slush may be increased by including an agitation feature such as at least one fin in one or more sidewalls of the slush bottle. The rotating slush bottle is chilled. One variation is to keep the sterile saline in a flexible container and tumble the flexible container in a rotating slush bottle. Other variations are suggested.

23 Claims, 11 Drawing Sheets

U.S. PATENT DOCUMENTS

| | | | |
|---|---|---|---|
| 4,669,274 A * | 6/1987 | Huang | 62/342 |
| 4,722,198 A * | 2/1988 | Huang | 62/342 |
| 4,813,243 A * | 3/1989 | Woods et al. | 62/381 |
| 4,934,152 A | 6/1990 | Templeton | |
| 5,163,299 A | 11/1992 | Faries, Jr. et al. | |
| 5,282,368 A * | 2/1994 | Ordoukhanian | 62/372 |
| 5,331,820 A | 7/1994 | Faries, Jr. et al. | |
| 5,333,326 A | 8/1994 | Faries, Jr. et al. | |
| 5,400,616 A | 3/1995 | Faries, Jr. et al. | |
| 5,402,644 A | 4/1995 | Faries, Jr. et al. | |
| 5,429,801 A | 7/1995 | Faries, Jr. et al. | |
| 5,457,962 A | 10/1995 | Faries, Jr. et al. | |
| 5,502,980 A | 4/1996 | Faries, Jr. et al. | |
| 5,522,095 A | 6/1996 | Faries, Jr. et al. | |
| 5,524,643 A | 6/1996 | Faries, Jr. et al. | |
| 5,551,240 A | 9/1996 | Faries, Jr. et al. | |
| 5,615,423 A | 4/1997 | Faries, Jr. et al. | |
| 5,653,938 A | 8/1997 | Faries, Jr. et al. | |
| 5,809,788 A | 9/1998 | Faries, Jr. et al. | |
| 5,816,252 A | 10/1998 | Faries, Jr. et al. | |
| 5,857,467 A | 1/1999 | Faries, Jr. et al. | |
| 5,862,672 A | 1/1999 | Faries, Jr. et al. | |
| 5,879,621 A | 3/1999 | Faries, Jr. et al. | |
| 5,950,438 A | 9/1999 | Faries, Jr. et al. | |
| 6,003,328 A | 12/1999 | Faries, Jr. et al. | |
| 6,035,855 A | 3/2000 | Faries, Jr. et al. | |
| 6,087,636 A | 7/2000 | Faries, Jr. et al. | |
| 6,091,058 A | 7/2000 | Faries, Jr. et al. | |
| 6,148,634 A | 11/2000 | Sherwood | |
| 6,255,627 B1 | 7/2001 | Faries, Jr. et al. | |
| 6,371,121 B1 | 4/2002 | Faries, Jr. et al. | |
| 6,802,802 B2 * | 10/2004 | Woog | 493/129 |
| 6,810,881 B2 | 11/2004 | Faries, Jr. et al. | |
| 6,860,271 B2 | 3/2005 | Faries, Jr. et al. | |
| 6,910,485 B2 | 6/2005 | Faries, Jr. et al. | |
| 6,910,801 B2 * | 6/2005 | Sasaki | 366/220 |
| 6,918,395 B2 | 7/2005 | Faries, Jr. et al. | |
| 7,176,030 B2 | 2/2007 | Faries, Jr. et al. | |
| 7,269,970 B2 * | 9/2007 | Robertson | 62/457.5 |
| 7,347,210 B2 | 3/2008 | Faries, Jr. et al. | |
| 7,350,373 B1 | 4/2008 | Faries, Jr. et al. | |
| 7,389,653 B2 | 6/2008 | Kasza et al. | |
| 7,418,966 B2 | 9/2008 | Faries, Jr. et al. | |
| 7,419,070 B2 * | 9/2008 | Cantwell et al. | 220/739 |
| 2005/0247169 A1 | 11/2005 | Faries, Jr. et al. | |
| 2006/0194324 A1 | 8/2006 | Faries, Jr. et al. | |
| 2006/0260443 A1 | 11/2006 | Faries, Jr. et al. | |
| 2007/0089753 A1 | 4/2007 | Faries, Jr. et al. | |
| 2008/0017292 A1 | 1/2008 | Gammons et al. | |

FOREIGN PATENT DOCUMENTS

| | | |
|---|---|---|
| WO | WO 96-12922 A1 | 5/1996 |
| WO | WO 2007-035419 A1 | 3/2007 |

OTHER PUBLICATIONS

Folger's Coffee Containers; two pages of images from Google obtained on Nov. 17, 2010 showing various views of large Folger's Coffee Containers that are not perfectly circular as there are features including finger grooves.

* cited by examiner though the need for aggressive mixing needs to be balanced with the need to maintain the integrity of the drape boundary because the drape also serves as a sterile barrier.

METHOD AND APPARATUS FOR PRODUCING SLUSH FOR SURGICAL USE

This application claims priority to and incorporates by reference co-pending U.S. Provisional Application No. 61/059,732 filed Jun. 6, 2008.

FIELD OF THE DISCLOSURE

This disclosure relates generally to the production of sterile slush for use in surgery.

BACKGROUND

Devices for producing sterile saline slush are known in the art. Sterile saline slush is used in a variety of surgical applications to slow organ and tissue metabolic rates thereby protecting organs from irreversible tissue damage during cardiac, neurological organ transplant, vascular, urologic and other complex surgeries. It is important that the slush has as smooth, spherical a configuration as possible to ensure atraumatic slush without sharp crystal edges that could puncture or damage human flesh or organs. The slush should have a substantially uniform consistency to maintain optimal thermodynamic cooling performance.

In both the surgical and non-surgical methods, slush production depends on the same basic thermodynamic phenomena. As ice grows from water that contains "impurities" the water produces a crystal matrix with the "impurities" dispersed into the interstices of the matrix. The term "impurities" are used because of the way they affect the water crystal matrix, however, they are often desirable and necessary components. In the case of non-surgical slush for drinks, the "impurities" are things like sugar and flavor mixes. In the case of surgical slush the "impurity" is salt. The impurities also provide nucleation sites that allow ice crystals to initially form. During the process of freezing a stagnant container of water with impurities, a boundary layer of slush (ice crystal in a fluid mixture) can form between a solid ice layer and a liquid water layer.

If during the freezing process the fluid mixture is mechanically agitated, small crystal formations are generated at the nucleation sites but size growth of the crystal matrix is inhibited because mechanical agitation prevents larger crystal growth. When these small crystals are suspended in the bulk fluid they form a slurry or slush. Mechanical agitation also helps keep the bulk fluid temperature more consistent and helps reduced large crystal growth that would otherwise occur at the fluid boundary (i.e. surface or container walls) where heat is typically being transferred out of the fluid.

In some prior art devices fluid is contained in a basin lined with a drape. Mechanical agitation of the fluid is provided by continually flexing the drape by lifting the drape from below with a pin or arm. The top of the basin is open to ambient air and the fluid is cooled via the metal walls and bottom that supports the drape. With this arrangement, flexing of the drape is essential to prevent large crystal formation in the fluid that is contact with the drape where heat is being transferred away from the fluid. The drape flexing also needs to be sufficient to keep the bulk mixture consistent and to keep the crystal suspended in the slush mixture. However, the need for aggressive mixing needs to be balanced with the need to maintain the integrity of the drape boundary because the drape also serves as a sterile barrier.

The integrity of the sterile field is very important during surgery. Any breach that might indicate that the sterile field has become contaminated is taken very seriously. A breach that is undiscovered for a period of time is especially troublesome as it is difficult to assess when the breach was created and whether it caused the patient to be exposed to contaminants while vulnerable during surgery. Thus it is no wonder that there may be grave concerns about the ongoing potential for breaches in the sterile field maintained by sterile drapes.

Other methods of creating slush had other shortcomings. One such method called for placing bags of sterile saline in freezers to freeze the sterile saline solution and then smashing the bag with a mallet to create slush. Such a method has a number of shortcomings including the risk of forming jagged ice crystals.

Another method called for the use of a frozen metal basin and chilled alcohol. This method involved pouring sterile saline inside the basin and scraping the side of the basin until sufficient slush is collected. The method produces slush, but is time consuming and resource intensive. Such a process does not scale well to provide a device that creates and maintains a significant amount sterile surgical slush.

SUMMARY OF THE DISCLOSURE

The present disclosure includes information about methods and apparatus for producing saline slush for surgical applications. One aspect of this disclosure teaches producing surgical saline slush in a rigid or semi-rigid, high integrity, sturdy container that resists punctures and leaks to better maintain a sterile barrier and does not rely on having on external object placed in the fluid to mix the slush. One type of sturdy container would be a container that could be sterilized and re-sterilized for several sterilization/use cycles. A container that is adapted for many sterilization/use cycles may be made of a durable material such as a metal.

Another type of sturdy container is a pre-sterilized single use container. Such a single use container may be made of a suitable polymer to hold down costs. This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that arise from this application.

Other systems, methods, features, and advantages of the disclosed teachings will be or will become apparent to one with skill in the art upon examination of the following figures and detailed description. It is intended that all such additional systems, methods, features and advantages be included within the scope of and be protected by the claims that are ultimately associated with this disclosure through the use of one or more non-provisional or non-United States patent applications that claim this disclosure as a priority document.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

DETAILED DESCRIPTION

Figure 1:
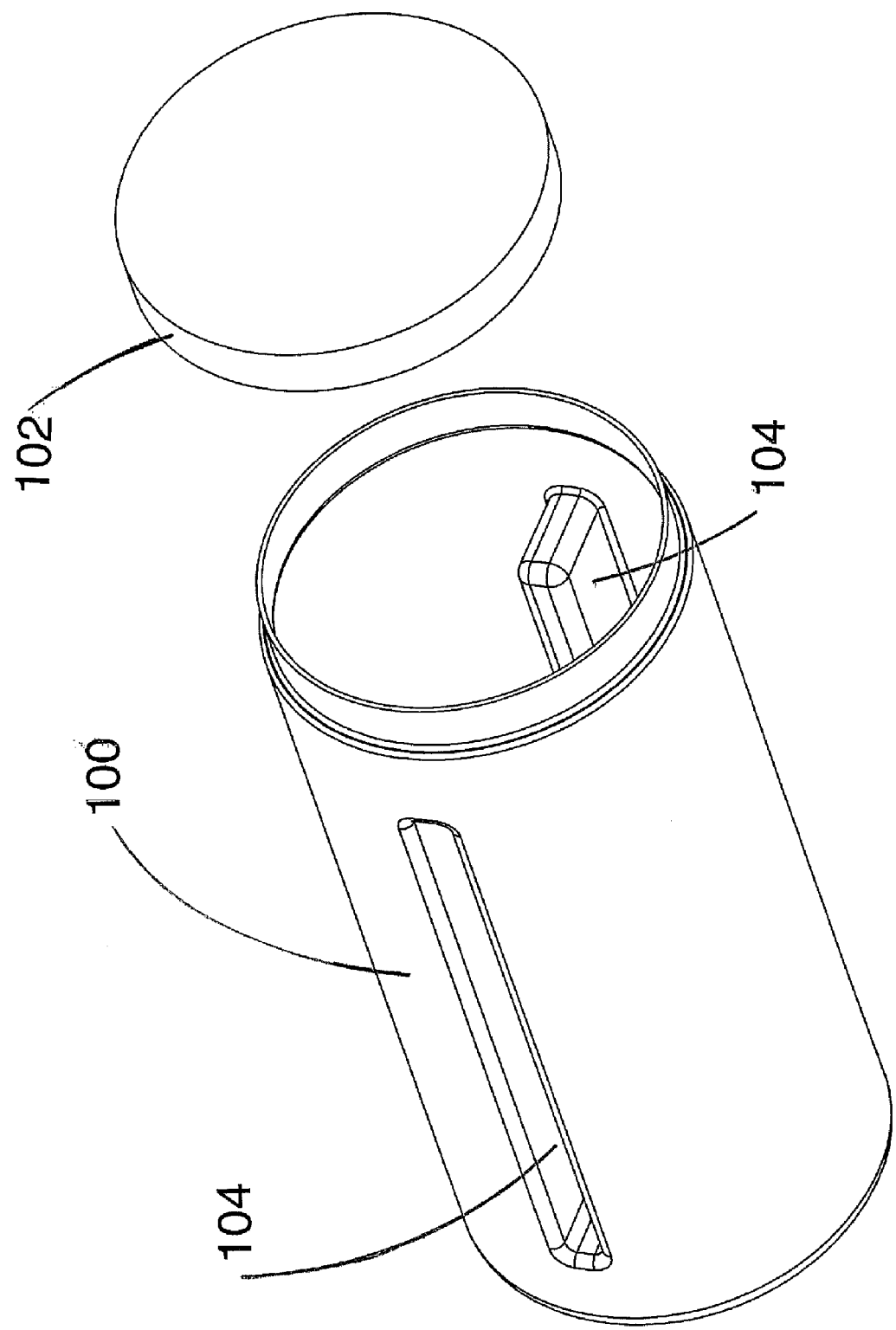
FIG. 1: Perspective view of a slush bottle and cap.

FIG. 1 illustrates a slush bottle 100 with a removable cap 102. The slush bottle 100 has a large mouth opening. The large mouth opening could be implemented with threads (not shown) for mating with corresponding threads (not shown) in the removable cap 102. Other reversible fastening techniques known to those of skill in the art could be used. Thus, bayonet fittings, snap tops, and other fastening methods, with or without the use of a gasket could be used. Implementations that use a slush bottle oriented away from horizontal and use less liquid so that the liquid does not reach the lid may have less stringent requirements for the lid.

During operation, the slush bottle 100 is initially filled with a liquid saline solution and has the removable cap 102 tightly secured. In this context, "filled" means filled to an intended fill line rather than totally filled as having the slush bottle only partially filled is useful in promoting the tumbling action described in more detail below.

The slush bottle 100 and cap 102 can be made of any of a number of conventional polymers having the appropriate mechanical properties and the ability to withstand the desired sterilization regime. An example of a suitable polymer material is polypropylene. (A reusable slush bottle may have a lid that is made of the same metal as the slush bottle or at least having a similar coefficient of thermal expansion.) The saline solution that is used is conventional sterile saline solution of the type used in surgical procedures whether heated to approximately body temperature or used at some other temperature.

Figure 2:
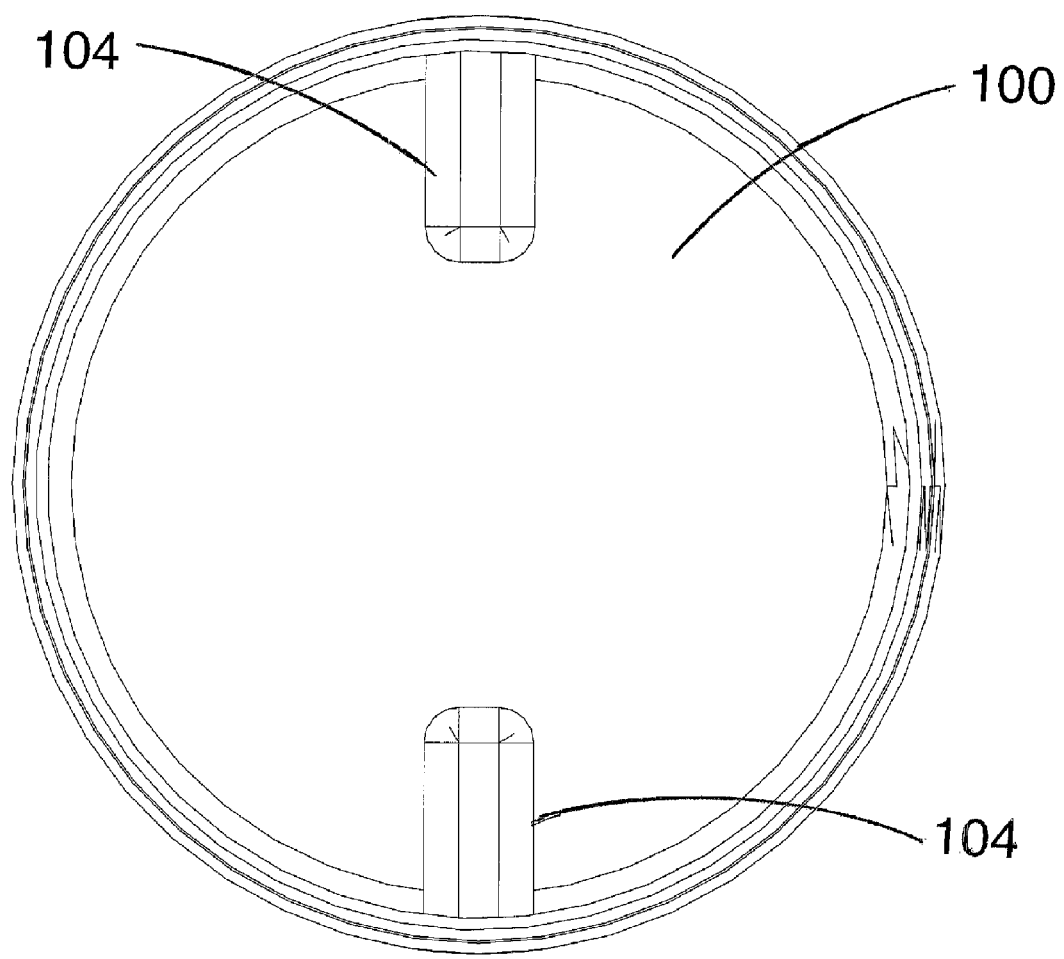
FIG. 2: Top view of a slush bottle showing the interior.

Two fins 104 (some might call them ribs) are formed into the side wall of the slush bottle 100 and protrude into the interior of the slush bottle 100. FIG. 2 shows a top view of the slush bottle 100 with interior fins 104. The slush bottle 100 shown in FIGS. 1 and 2 has two fins 104; however, one fin or more than 2 fins are also possible. While the two fins shown in FIGS. 1 and 2 are identical, the do not have to be. The fins may optionally have one or more gaps in the fin. When using fins with at least one gap, not all fins need to have gaps and not all fins need to have the same arrangement or spacing of the gaps. As the slush bottles rotate, the gaps in the fins will cause movement of the slush through the gaps relative to the slush that is lifted by the fin and tumbled. This will add another aspect to the stirring of the slush. Likewise the fins 104 do not need to be evenly spaced around the perimeter of the slush bottle 100. For example, the two fins 104 shown in FIG. 2 could be spaced a hundred degrees apart rather than being 180 degrees apart. Bottles with shapes other than cylindrical (i.e. oval, square, rectangular, etc.) are also possible.

While the fins shown in FIGS. 1 and 2 extend inward from the side wall, a slush bottle may optionally have one or more bottom protrusions that extend upward from the bottom of the slush bottle (towards the lid). To the extent that the protrusion is at least partially non-symmetric with the center axis of the bottom of the slush bottle, the protrusion will add another dimension to the mixing of the slush, will potentially add another surface for the falling slush to strike and may provide a way to enhance the cooling of water to form slush to the extent that cooled air is present in the protrusion extending into the slush bottle.

While not strictly required, it is felt that a fin that is hollow and open to the air external to the slush bottle will help cool air enter the fin and augment the cooling. A secondary benefit of the fin and a design consideration for the fins is the hollow fin may provide a finger hold for a user that is picking up a frosty slush bottle from the slush making device. The hollow fin may help the user have a reliable grip on the slush bottle while lifting, removing the cap, and pouring the slush.

The slush bottle geometry with at least one interior fin allows slush to be directly produced in the enclosed slush bottle interior when the slush bottle is placed in a cold enough environment and the slush bottle is agitated. Agitation could come from rotating the long axis of the slush bottle while the axis is at or near horizontal. The range of acceptable tilt angles from horizontal upward would be a function of a number of factors. Unless the bottom has one or more protrusions, it may be beneficial for the saline water to be loaded into the slush bottle so that at least some air can reach the bottom of the slush bottle so that there is some level of tumbling all the way to the bottom. The deviation from horizontal that would work would be a function of the aspect ratio of the slush bottle and the relative height of the fill line of a slush bottle relative to the height of a slush bottle when placed in a vertical position.

One of skill in the art will appreciate that if the slush bottle lid provided a water tight seal and the slush bottle could be retained in the slush creating device while the slush bottle is rotated that the slush bottle lid could be lower than the slush bottle bottom thus below horizontal.

In the configuration shown in FIG. 1, the fins 104 introduce mechanical agitation to the solution by carrying fluid and/or slush up the sidewall during rotation. Once the fin rotates above the horizontal plane, the fluid and/or slush the fin was carrying runs or falls back into the bulk mixture. (Note that if the fill level is above the horizontal plane the run-off for liquids may be delayed until the fin is above the waterline but slush will move relative to other slush in many instances when the fin gets above horizontal.) This agitation keeps the solution mixed and tends to promote an even temperature distribution. This agitation also breaks up larger crystal matrices to promote the creation and maintenance of a fine slush mixture (as opposed to coarse). Falling material works to breaks off crystals that form along the slush bottle interior.

The amount of agitation provided to the slush may be reduced if the slush bottle 100 is positioned in a vertical orientation in the slush bottle carriage (or even 180 degrees rotation from vertical). Thus in most instances the slush bottle carriage should be oriented so that the slush bottle is neither substantially vertical nor substantially upside down.

Having a slush bottle opening that is large relative to the cross section of the slush bottle is desirable. The large mouth opening of the slush bottle makes it easy to pour the slush out of the container. A small opening (relative to the cross section of the slush bottle) might encourage the fine, loosely packed slush to become compacted as the slush passes through a reduced cross sectional area as the slush cannot easily move from a larger cross sectional area to a smaller cross sectional area without being compacted. If the slush gets compacted, the slush tends to behave more like a solid and is therefore even harder to make the slush exit through a small opening.

Figure 3:
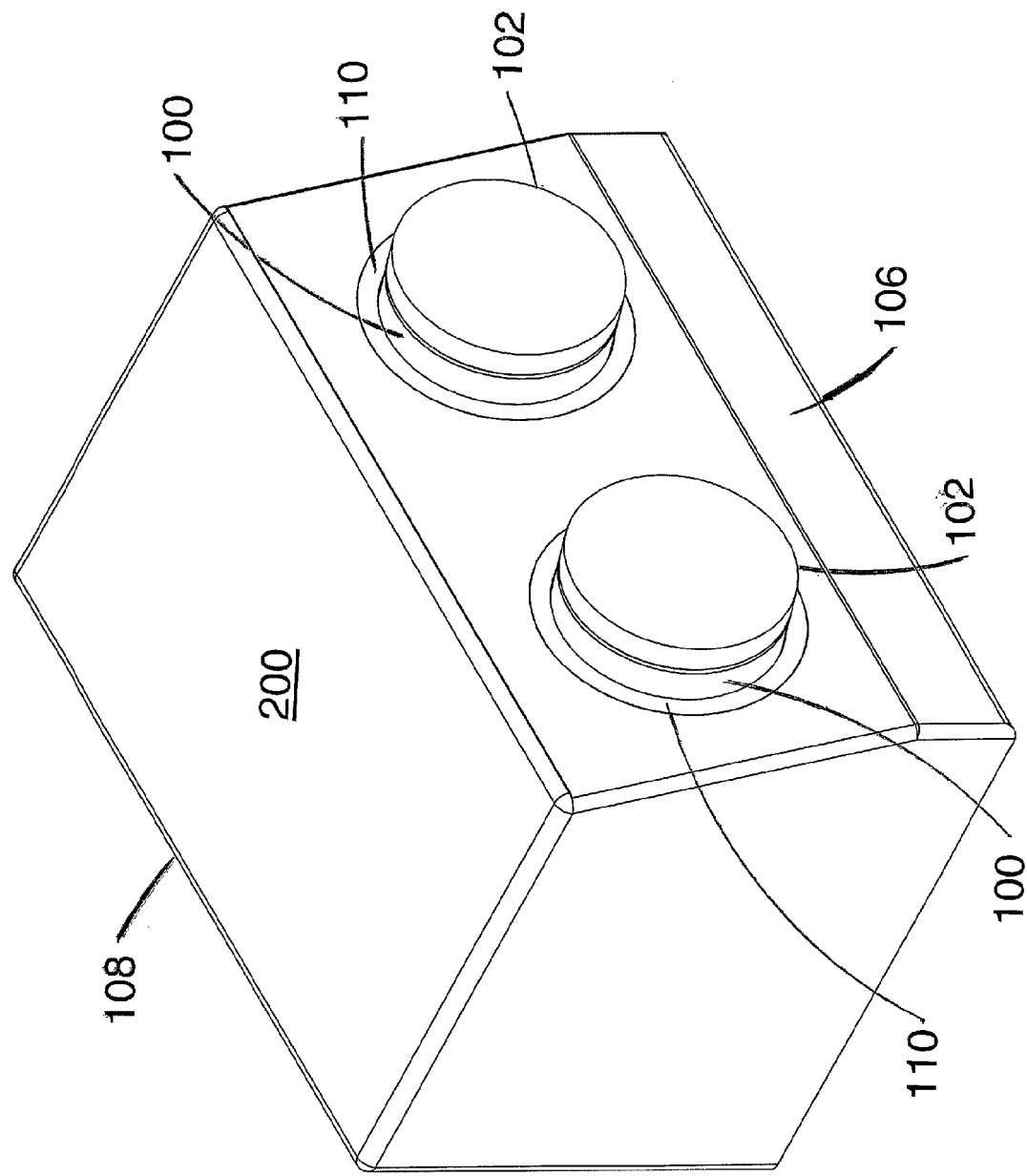
FIG. 3: View of slush production device with covers.

FIG. 3 illustrates an example embodiment of a device 200 that can rotate and cool a slush bottle 100 with a cap 102 in the manner described above so as to turn the enclosed fluid saline solution into a slush mixture. While it is important that the interior of the slush bottle and the water/slush mixture remain sterile, it is not important that the outside of the slush bottle remain sterile during the chilling process. Thus, it is not important to design or maintain the device 200 so that the interior of the device remain sterile.

In this embodiment, the device 200 is designed to hold two slush bottles 100 that are slid into the device 200 through rotating outer rings 110. The rotating outer rings 110 can rotate relative to the stationary outer support frame 106. The device 200 is enclosed with a top cover 108 (also known as a housing).

While the device 200 can receive and chill two slush bottles 100, devices (not shown) may be adapted receive only one slush bottle, or conversely may be adapted to receive and chill more than two slush bottles. In most instances, a device with an open cavity that allows chilled air to flow around multiple slush bottles will need to have an empty slush bottle inserted into each slush bottle hole or some sort of cover in order to reduce the loss of cold air out of an opening that does not have an inserted slush bottle.

An alternative would be to have separate cooling for separate compartments so that if a multi-bottle device had only one slush bottle inserted for cooling, only the compartment around that slush bottle would be cooled and the cooling going to that compartment would not travel by convection into one or more adjacent compartments that do not have a slush bottle to cool.

The device 200 in FIG. 3 is shown as a stand-alone device. One of ordinary skill in the art can appreciate that this functionality may be built into a device with other functionality such as a device intended to maintain sterile fluid at an elevated temperature for use in medical procedures. See for example commonly assigned U.S. Pat. No. 7,128,275 for Liquid Warming Device with Basin or Patent Application Publication No. 2006/0289016 for Open Access Sleeve for Heated Fluid Units.

Figure 4:
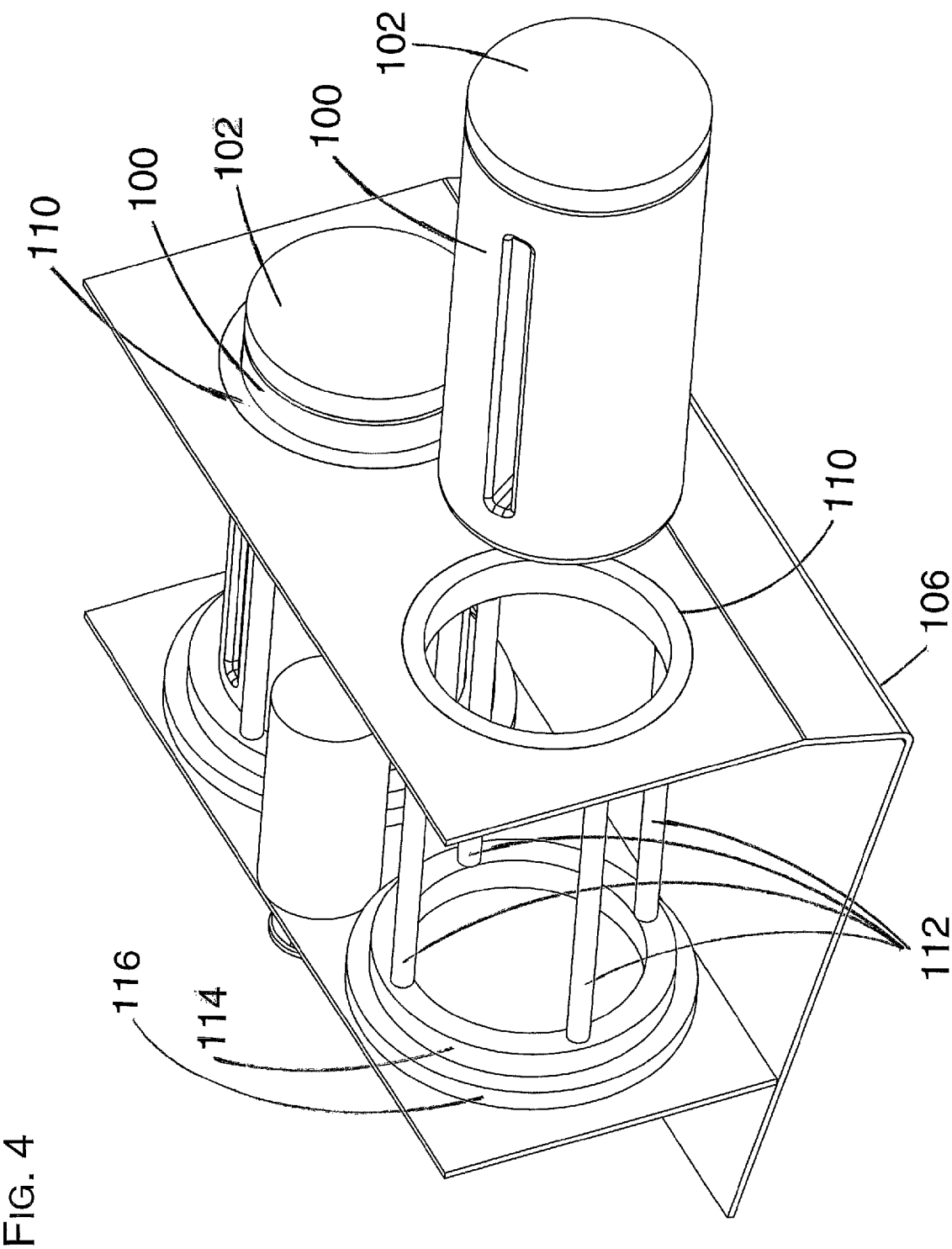
FIG. 4: Front perspective view of device without covers.

FIG. 4 shows the device 200 with the top cover 108 removed and with one of the slush bottles 100 withdrawn from the device 200. One end of each of four connector rods 112 is attached to the back side of the rotating outer ring 110. The other end of each of the four connector rods 112 is connected to the rotating bottom ring 114. The rotating outer ring 110, the connector rods 112, and the rotating bottom ring 114 all rotate together and are supported by a bottom bearing 116 on one side and a front bearing 118 (shown later in FIG. 5). The bottom bearing 116 is mounted in the back support plate 120 and the front bearing 118 is mounted in the outer support frame 106.

Figure 5:
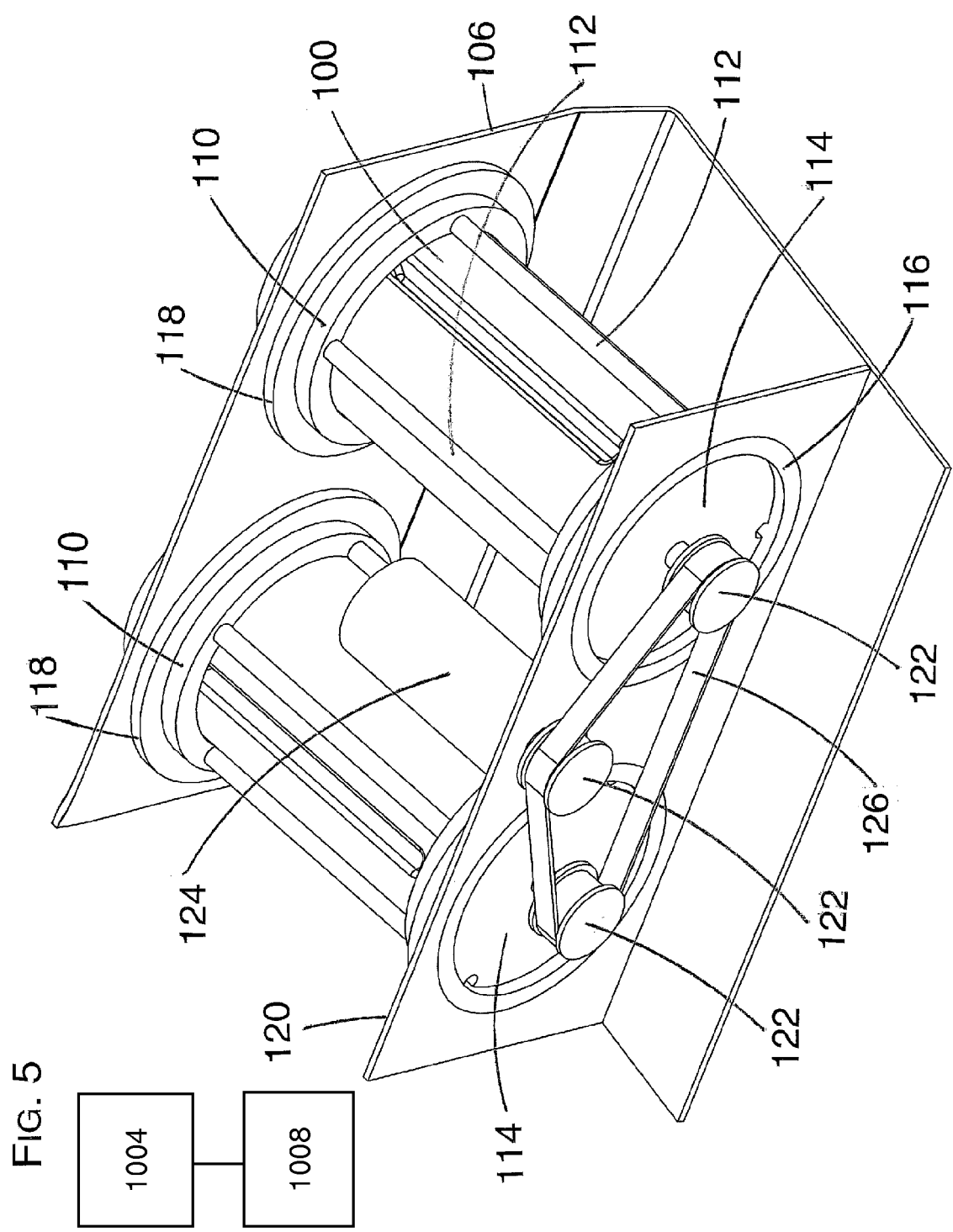
FIG. 5: Back perspective view of device without covers.

FIG. 5 is a view of the device 200 from the back. The front bearing 118 described above can be seen mounted in the outer support frame 106 and holding the rotating outer ring 110. A drive pulley 122 is attached to both rotating bottom rings 114 and to the drive motor 124. The drive motor 124 is mounted to the back support plate 120. A drive belt 126 is looped around the three drive pulleys 122. Visible in this figure are some of the notches that provide access to the fasteners used to retain the individual connector rods. These details are routine to those of skill in the art and need no further discussion.

When the drive motor 124 is turned on it causes both rotating bottom rings 114 to rotate via the drive belt 126 and drive pulley 122. This in-turn cause the slush bottles 100 to rotate because they are supported by the rotating bottom ring 114, the connector rods 112, and the rotating outer ring 110 which are being driven by the drive motor 124. The slush bottles may be rotated at a relatively slow speed so as to facilitate the dropping of material to agitate and to minimize any centrifuge effect that would impede such agitation. Typical rotation speeds would be in the range of 10 to 30 slush bottle rotations per minute, however, a broader or shifted range of speeds may be adequate in some situations.

One of ordinary skill in the art will appreciate the minor modifications necessary to the device 200 to receive and rotate slush bottles with a cross section that is something other than round. One of ordinary skill in the art will recognize that other choices and arrangement of components could be made in order to effect the rotation of the slush bottles. For example the driver motor 124 could be located outside of the enclosed space.

The individual components of the cooling system 1004 (FIG. 5) along with the interior covers and insulation are not shown in the figures because they would obscure the drive and support components. The cooling system's purpose is to provide chilled air to surround the slush bottles and to chill the air below the freezing point of the saline water within the slush bottles. The cooling system may include one or more devices such as fans to circulate the cooled air to promote the rapid cooling of the saline in the one or more bottles. Those of skill in the art will appreciate that a range of cooling systems could be used including but not limited to a standard compressor type system or a solid state Peltier cooling system.

The cooling system regulates the temperature around the slush bottles to within a specified range to allow slush to be produced and maintained. The control system 1008 may simply seek to maintain the air within the device at a particular target temperature that is at or slightly below the freezing point for sterile saline solution of a particular salinity. A more sophisticated system would have an initial target temperature that is well below the freezing point to expedite the initial production of slush but then have a separate maintenance temperature intended for use when the slush is ready. This maintenance temperature could be at or slightly below the freezing point (to compensate for thermal losses and energy input to the system). As the slush will continue to freeze slowly at this freezing point, it may be useful to build in a capacity for the target temperature to drift above and below the freezing point (as with a normal two temperature control scheme that results in a saw tooth temperature profile).

In some instances, increasing the level of agitation, perhaps by increasing the speed of slush bottle rotation may provide a wider range of temperatures that may be used to maintain the slush as slush.

The device 200 may optionally have a stop button to stop the rotation of the slush bottles. This stop button may make it easier to remove a slush bottle from the slush making device.

Additional Views of the Slush Bottle.

FIGS. 6-9 show the slush bottle 100 from FIGS. 1 and 2 from four view separated by 90 degrees.

Figure 6:
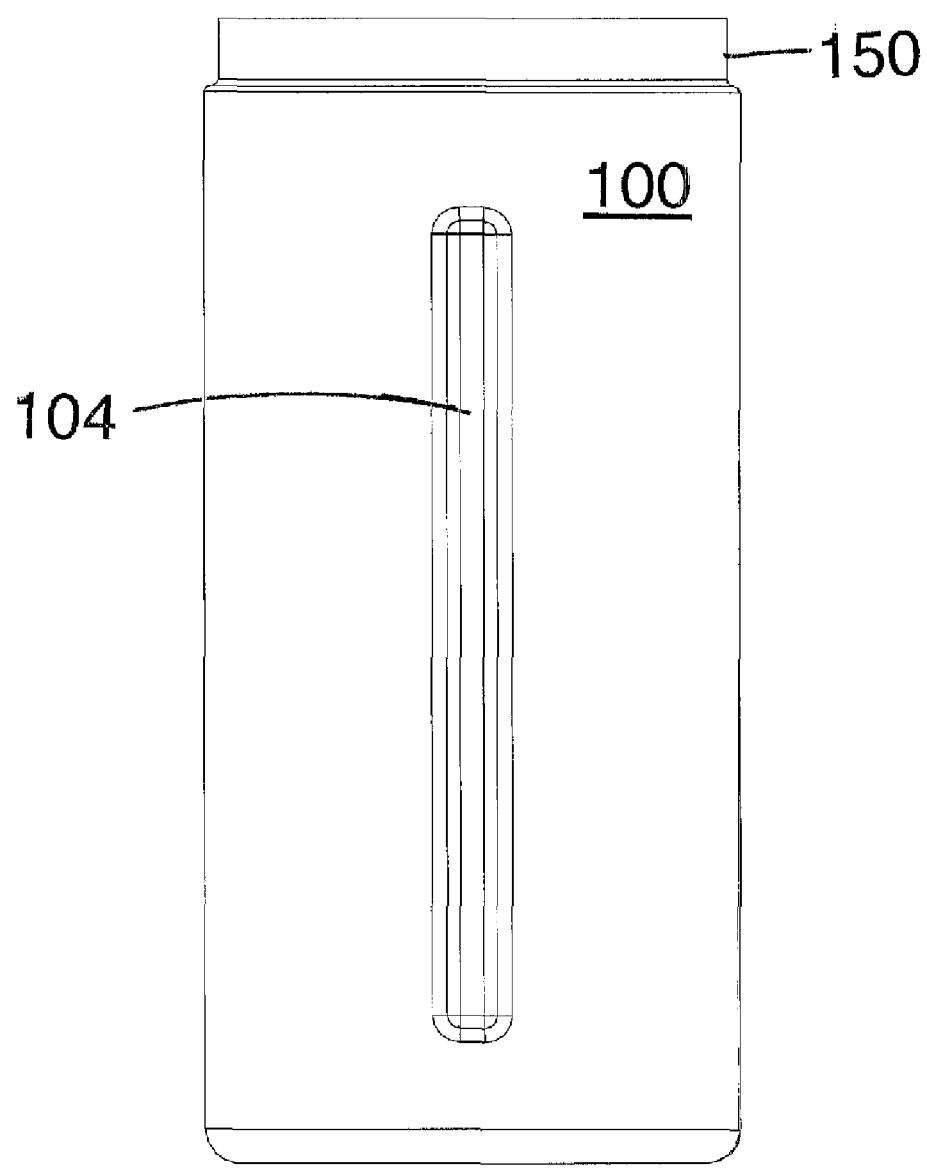
FIG. 6: Side view of the slush bottle of FIGS. 1-4.

FIG. 6 shows a side view of the slush bottle 100 with the interior of one fin 104 visible. The portion 150 of the slush bottle that receives the cap (seen in FIG. 1) is visible.

Figure 7:
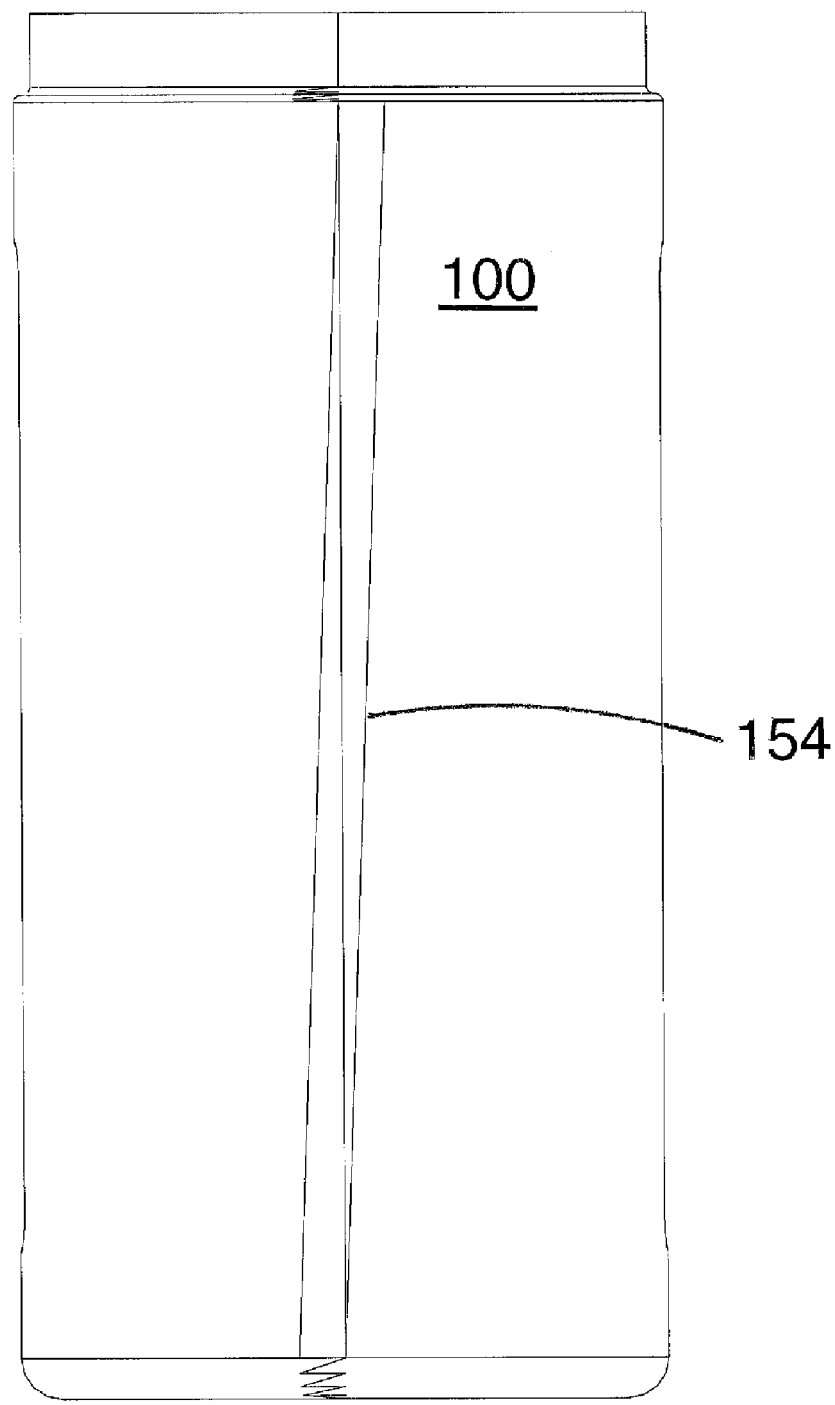
FIG. 7: Side view of the slush bottle 90 degrees offset from FIG. 6.

FIG. 7 shows a side view of the slush bottle 100 90 degrees offset from FIG. 6. Visible in this figure is a representation of a bottle seam 154. The actual bottle seam may not appear as shown in FIG. 7 and may not be readily apparent to an untrained eye.

Figure 8:
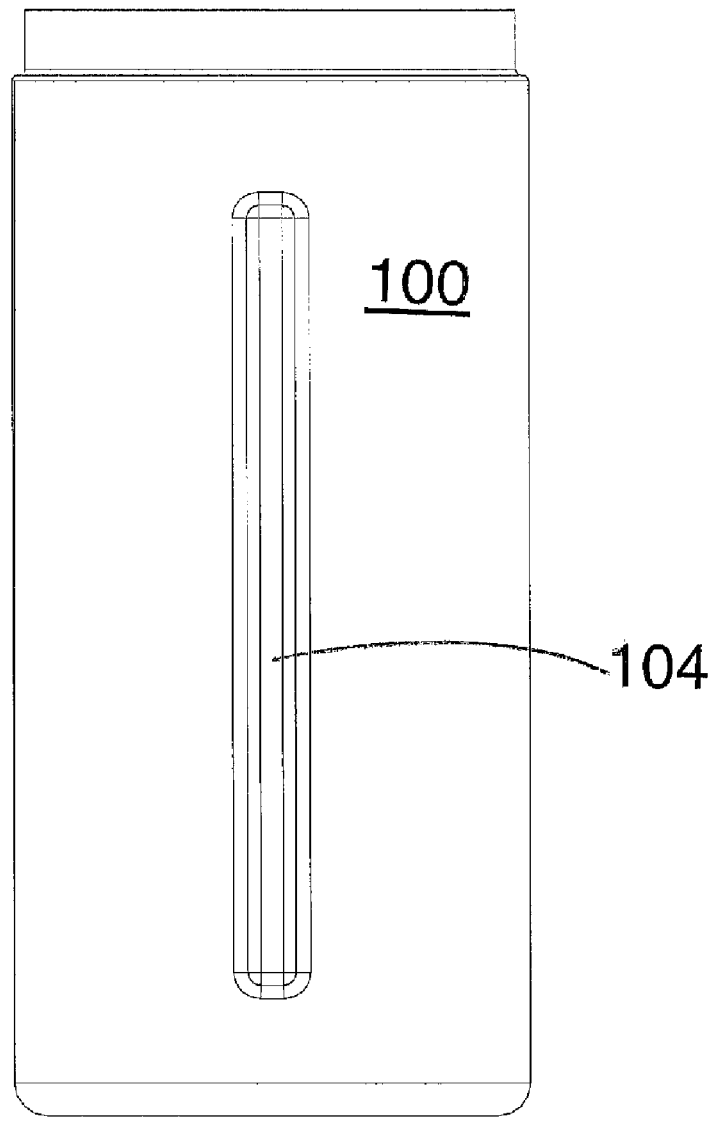
FIG. 8; Side view of the slush bottle 90 degrees offset from FIG. 7 and 180 degrees offset from FIG. 6.

FIG. 8 shows a side view of the slush bottle 100 90 degrees offset from FIG. 7. FIG. 8 is identical to FIG. 6 because this particular implementation of the slush bottle has two identical fins offset by 180 degrees.

Figure 9:
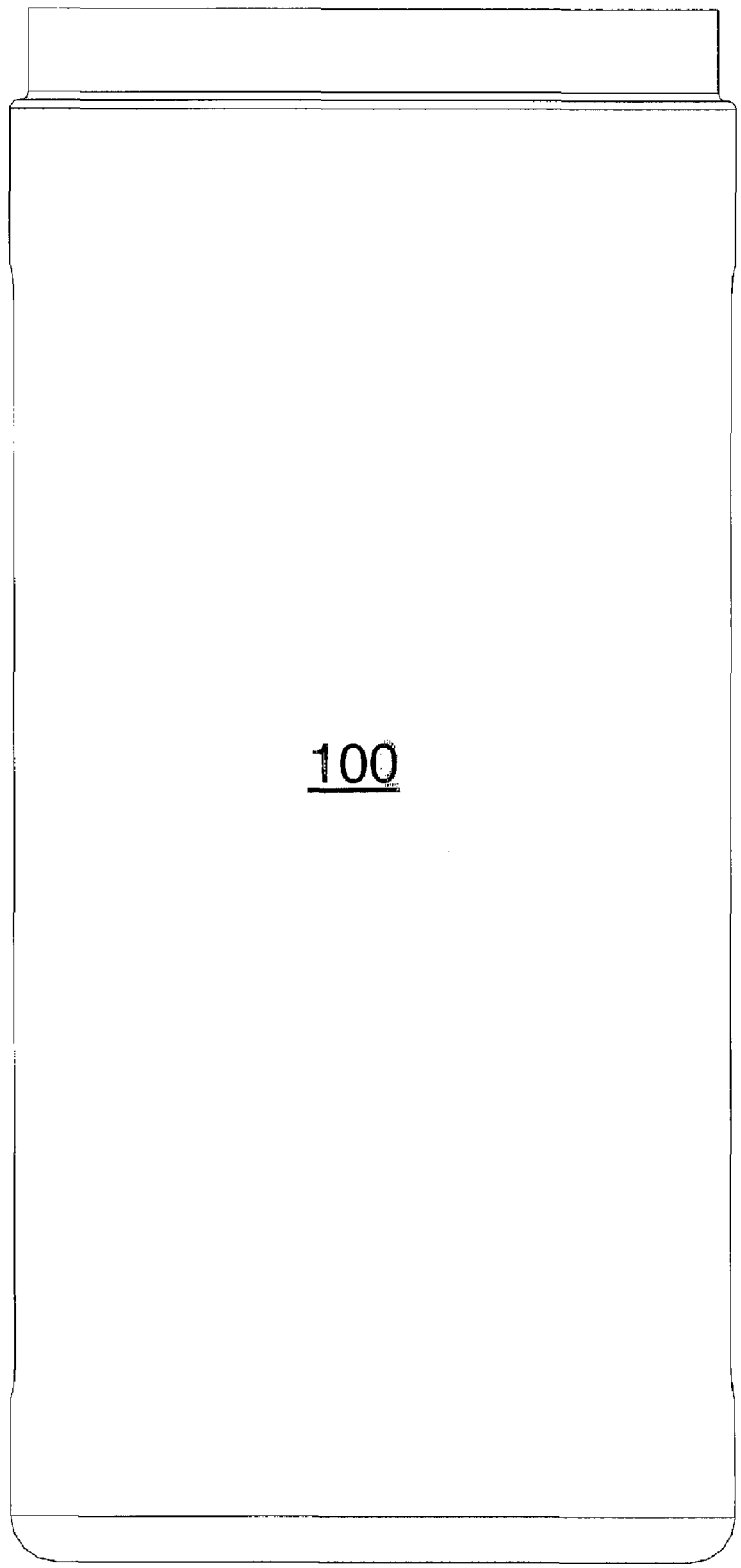
FIG. 9: Side view of slush bottle 90 degrees offset from FIG. 8.

FIG. 9 shows a side view of slush bottle 100 90 degrees offset from FIG. 8.

Figure 10:
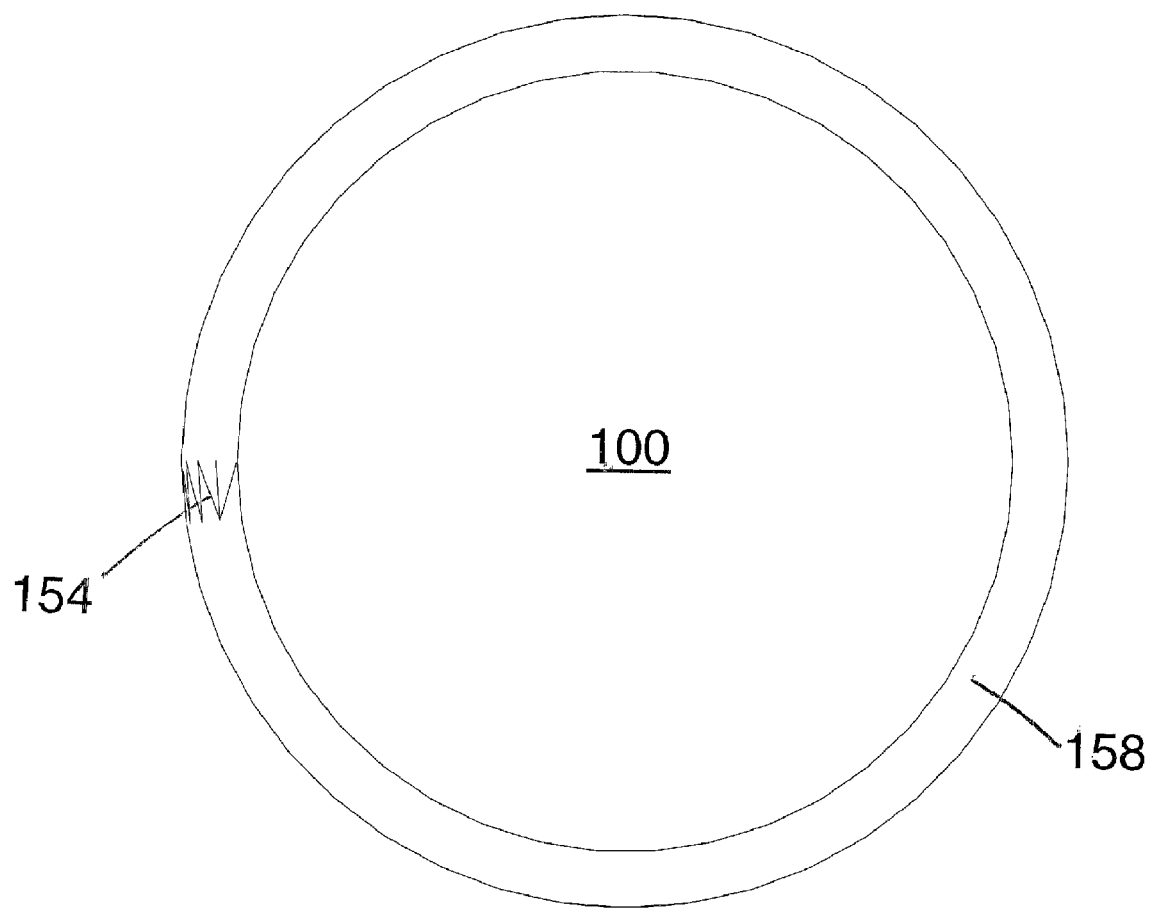
FIG. 10: A bottom view of slush bottle shown in FIGS. 1-10.

FIG. 10 shows a bottom view of slush bottle 100 including beveled rim 158 and the bottom of the representation of the bottle seam 154.

Alternatives, Variations, and Extensions.

Cabinet Doors.

The slush production device 200 shown in FIGS. 4-6 has the end of the slush bottle 100 and the slush bottle cap 102 protruding beyond openings in the device top cover 108 (also known as a housing). The slush bottle 100 and slush bottle cap 102 are thus part of the effective border that holds the chilled air within the device 200. One of ordinary skill in the art will appreciate that the device could be modified to have a larger enclosed volume that is accessed through cabinet doors or other ready access options known in the art. Thus, the cabinet doors would form the barrier between the chilled air used for cooling and the ambient air in the hospital. Note that if the slush bottle was contained within a housing with closed cabinet doors, one could conceivably maintain a sterile state within the housing and operate the slush making device using a slush bottle without a top. Obviously the slush bottle orientation and fill level would need to be adjusted that that saline would not splash out the top during slush operation. This variation is unlikely to be widely adopted.

Non-Centerline Center of Rotation.

The slush production device 200 shown in FIGS. 4-6 has a center of rotation for rotating the slush bottle 100 that runs through the axial centerline of the slush bottle 100. This configuration may be preferred in some embodiments as it would tend to provide a smooth uniform agitation. Other embodiments may use a center of rotation that runs through something other than the top/bottom centerline of the slush bottle. An advantage of this choice may include a more complex agitation pattern.

Multi-Angled Bottle Walls.

One of skill in the art will recognize that a slush bottle made with severe wall joint angle changes may provide much of the agitation provided by the slush bottles with fins shown above. For example, a slush bottle with the cross section of a triangle or a five or six sided star might provide adequate agitation, particularly if the slush bottle was oriented closer to horizontal to promote slush from falling from the ridges formed by the points of the star or other appropriate shape.

Saline Within a Flexible Bag.

Figure 11:
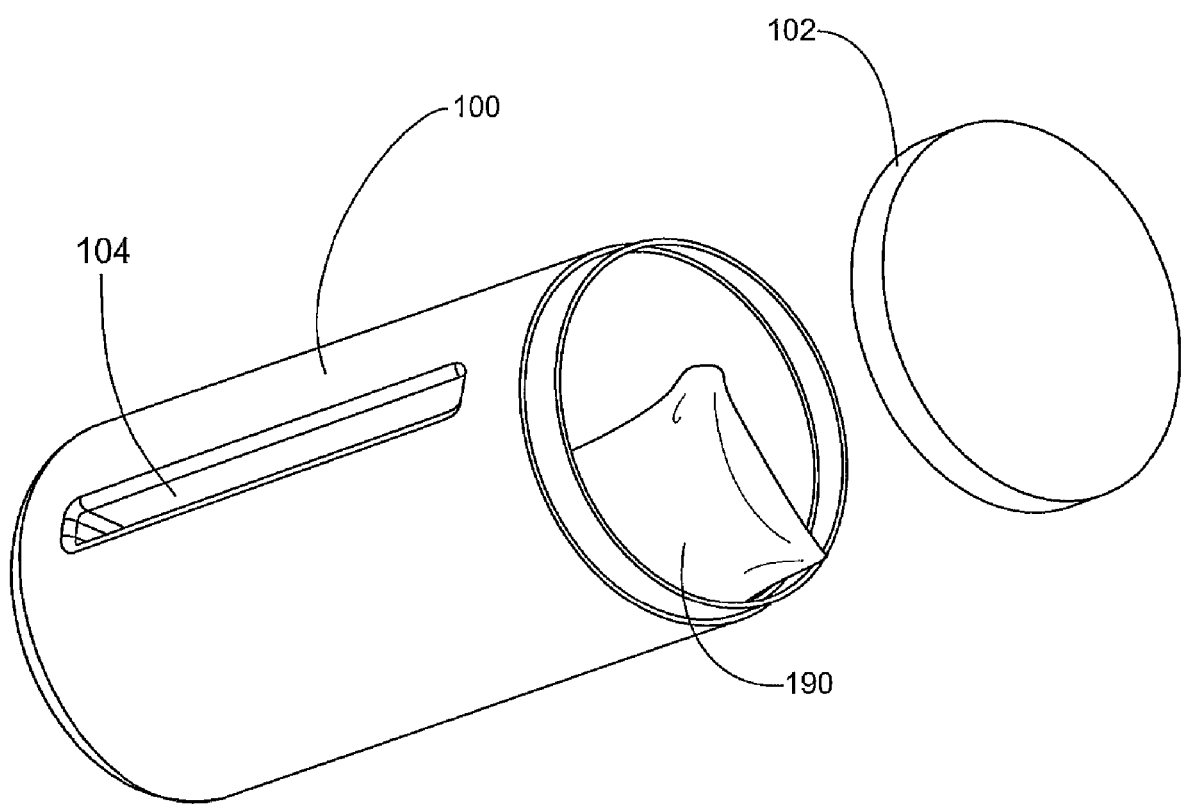
FIG. 11 shows a flexible container of sterile saline in a slush bottle.

An alternative implementation would be to place saline in a flexible container of any shape. It is probably easiest to envision a clear bag like a partially filled IV bag. Ideally the bag should not be so filled with saline as to be taut. The saline bag 190 may be placed in a slush bottle 100 as shown in FIG. 11 and tumbled as the slush bottle rotates in the slush bottle carriage. The bag would need to be sufficiently robust, including any seams and broad pour spouts to handle the tumbling within the slush bottle which may be aligned close to horizontal.

One of ordinary skill in the art will recognize that in a saline bag implementation, the slush bottle need not be removable but may be integrated within the slush producing device much like the horizontal drum of a clothes dryer.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

What is claimed is:

1. A system for production of sterile saline slush for use in medical procedures, the system comprising:
    a device comprising:
        a housing to define an interior of the device from an exterior of the device, the housing having at least one opening for receipt of a slush bottle, the slush bottle receiving a flexible container containing sterile saline solution; and
        an assembly to receive the slush bottle and to rotate the slush bottle along an axis of rotation to agitate a slush/saline slurry within the slush bottle as the slush bottle is rotated while exposed to air cooled sufficiently to freeze the saline solution placed in the slush bottle and;
        wherein the slush/saline slurry within the slush bottle is contained within the flexible container that tumbles as the slush bottle rotates.

2. A method for making sterile saline slush; the method comprising:
    partially filling a sterile slush bottle with sterile liquid saline and putting a removable top on the slush bottle so that the slush bottle contains sterile liquid saline and air;
    maintaining the removable top of the slush bottle at an incline relative to a bottom of the slush bottle so that the removable top and the bottom of the slush bottle are not maintained in a vertical relationship; and
    rotating the slush bottle along an axis of rotation as at least a portion of the slush bottle is exposed to air cooled below a freezing temperature for the sterile liquid saline contained in the slush bottle to form a slush/saline slurry, the rotating slush bottle having at least one agitation feature in at least one side wall of the slush bottle to lift slush from the slush/saline slurry and allow the slush to fall to reduce large crystal growth as the slush bottle is rotated.

3. The method of claim 2 wherein the act of maintaining the removable top of the slush bottle at the incline relative to the bottom of the slush bottle includes inserting the slush bottle into a slush bottle carriage by opening a housing that surrounds the slush bottle carriage and closing the housing after inserting the slush bottle into the slush bottle carriage.

4. The method of claim 2 wherein the at least one agitation feature is at least one fin that extends inward from the at least one side wall.

5. The method of claim 2 wherein the slush bottle including the top of the slush bottle is placed within a cooling device housing and the cooling device housing is closed so that chilled air is provided to adjacent to the removable top of the slush bottle.

6. The method of claim 2 wherein rotating the slush bottle along the axis of rotation as at least the portion of the slush bottle is exposed to air cooled below a freezing temperature for the sterile liquid saline contained in the slush bottle includes periodically allowing the cooled air to rise in temperature above the freezing temperature for sterile surgical slush contained in the slush bottle as a control system allows for a movement of a target temperature for the cooled air.

7. A method for making sterile saline; the method comprising:
    partially filling a sterile slush bottle with sterile liquid saline and putting a removable top on the slush bottle so that the slush bottle contains sterile saline and air;
    maintaining the removable top of the slush bottle at an incline relative to a bottom of the slush bottle so that the removable top and bottom of the slush bottle are not maintained in a vertical relationship; and rotating the slush bottle along an axis of rotation as at least a portion of the slush bottle is exposed to air cooled below a freezing temperature for the sterile saline contained in the slush bottle to form a slush/saline slurry, the rotating slush bottle having at least one agitation feature in at least one side wall of the slush bottle to lift slush from the slush/saline slurry as the slush bottle is rotated and the rotating slush bottle allows slush to tumble downward to produce slush with a smooth spherical configuration.

8. A method for making sterile saline slush for use in a medical procedure; the method comprising:

partially filling a sterile slush bottle with sterile liquid saline and putting a top on the slush bottle so that the slush bottle contains sterile saline and air;

inserting the slush bottle into a device for production of sterile saline slush such that the top-bottom axis of the slush bottle is at an oblique angle with respect to horizontal;

rotating the slush bottle along an axis of rotation as at least a portion of the slush bottle is exposed to air cooled below a freezing temperature for the sterile saline contained in the slush bottle, the rotating slush bottle having at least one agitation feature in at least one side wall of the slush bottle to agitate a slush/saline slurry as the slush bottle is rotated and the rotating slush bottle allows slush to tumble downward;

wherein the at least one agitation feature has a path for chilled air outside the slush bottle to enter the at least one agitation feature to cool the agitation feature; and making sterile saline slush created in the slush bottle available for use in a medical procedure.

9. A method for making sterile saline slush for use in a medical procedure; the method comprising:

partially filling a sterile slush bottle with sterile liquid saline and putting a top on the slush bottle so that the slush bottle contains sterile liquid saline and air;

inserting the slush bottle into a cooling device housing such that a top-bottom axis of the slush bottle is not vertical;

rotating the slush bottle along an axis of rotation as at least a portion of an exterior of the slush bottle is exposed to air cooled below a freezing temperature for the sterile liquid saline contained in the slush bottle, the rotating slush bottle having at least one agitation feature in at least one side wall of the slush bottle to agitate a slush/saline slurry as the slush bottle is rotated; and making sterile saline slush created in the slush bottle available for use in a medical procedure;

wherein the top of the slush bottle protrudes from the cooling device housing as the slush bottle is rotating; and making sterile saline slush created in the slush bottle available for use in the medical procedure is achieved by:

lifting the slush bottle from the cooling device housing, removing the top from the slush bottle, and pouring the sterile saline slush.

10. The method of claim 9 wherein making sterile saline slush created in the slush bottle available for use in a medical procedure includes removing the slush bottle without mechanically decoupling a drive mechanism used for rotating the slush bottle.

11. The method of claim 9 wherein the step of making sterile slush available for use in the medical procedure includes stopping the rotation of the slush bottle.

12. A method for making sterile saline slush for use in a medical procedure; the method comprising:

placing a flexible container of sterile saline into a slush bottle so that there is sufficient room for the flexible container to tumble within the slush bottle;

inserting the slush bottle into a device for production of sterile saline slush such that the top-bottom axis of the slush bottle is not vertical;

rotating the slush bottle along an axis of rotation as at least a portion of the slush bottle is exposed to air cooled below a freezing temperature for the sterile saline contained in the slush bottle, the rotating slush bottle having at least one agitation feature in at least one side wall of the slush bottle to agitate a slush/saline slurry in the flexible container as the slush bottle is rotated; and making sterile saline slush created in the flexible container available for use in a medical procedure.

13. A device for production of sterile saline slush, the device comprising:

a housing to define an interior of the device from an exterior of the device, the housing having at least one opening for receipt of a slush bottle;

an assembly to receive the slush bottle and to rotate the slush bottle along an axis of rotation to agitate a slush/saline slurry within the slush bottle as the slush bottle is rotated while exposed to air cooled sufficiently to freeze a saline solution placed in the slush bottle and;

the slush bottle having:

a removable top;

a slush bottle body having a bottom and a set of one or more side walls such that with the addition of the removable top, the slush bottle is sealed; and at least one feature in the set of one or more side walls that agitates the slush/saline slurry within the slush bottle as the slush bottle is rotated;

wherein the device for production of sterile saline slush maintains the removable top of the slush bottle at an incline relative to the bottom of the slush bottle so that the removable top and bottom of the slush bottle are not maintained in a vertical relationship and rotation of the slush bottle causes the at least one feature in the set of one or more side walls to lift slush from the slush/saline slurry and allows the slush to fall to reduce large crystal growth.

14. The device of claim 13 wherein the housing has at least one opening to allow the slush bottle to be partially inserted into the housing and into the assembly while the removable top of the slush bottle is outside the housing.

15. The device of claim 14 wherein the device has at least two openings to allow two slush bottles to be partially inserted into the housing, each slush bottle into a separate assembly, while the removable top of each slush bottle is left outside the housing.

16. The device of claim 13 wherein the housing may be opened to allow the insertion of at least one complete slush bottle with a corresponding removable top of the slush bottle and the housing may be closed to envelope the at least one complete slush bottle and removable top.

17. The device of claim 13 wherein the at least one feature in the set of one or more side walls is a fin that extends inward from the side wall to agitate the slush/saline slurry within the slush bottle as the slush bottle is rotated.

18. The device of claim 17 wherein the fin is hollow and open to the outside of the slush bottle such that air may enter the fin from an exterior of the slush bottle to help cool the fin.

19. The device of claim 13 wherein the at least one feature in the set of one or more walls is a set of one or more severe wall joint angles.

20. The device of claim 13 wherein the slush bottle is a sterilized polymer such that placement of sterile saline within the interior of the slush bottle maintains the sterile saline as sterile saline.

21. The device of claim 13 wherein the slush bottle is made from a material capable of more than one sterilization and use cycle.

22. The device of claim 13 further comprising a control system for controlling a cooling system to set a target temperature that moves over time to alternate above and below a freezing point for sterile surgical slush.

23. A device for production of sterile saline slush, the device comprising:
   a housing to define an interior of the device from an exterior of the device, the housing having at least one opening for receipt of a slush bottle;
   a slush bottle carriage to receive the slush bottle and to rotate the slush bottle along an axis of rotation to agitate a slush/saline slurry within the slush bottle as the slush bottle is rotated while exposed to air cooled sufficiently to freeze a saline solution placed in the slush bottle and;
   the slush bottle having:
      a removable top;
      a slush bottle body having a bottom and a set of one or more side walls such that with the addition of the removable top, the slush bottle is sealed; and
      at least one feature in the set of one or more side walls that agitates the slush/saline slurry within the slush bottle as the slush bottle is rotated by the slush bottle carriage;
   wherein the slush bottle carriage maintains the removable top of the slush bottle at an incline relative to the bottom of the slush bottle so that the removable top and bottom of the slush bottle are not maintained in a vertical relationship and rotation of the slush bottle carriage causes the at least one feature in the set of one or more side walls to lift slush from the slush/saline slurry and allows the slush to fall through air in the slush bottle to produce slush with a smooth spherical configuration.

* * * * *